United States Patent [19]

Himmler et al.

[11] Patent Number: 4,795,788

[45] Date of Patent: Jan. 3, 1989

[54] PROCESS FOR THE SELECTIVE HYDROGENATION OF UNSATURATED POLYMERS CONTAINING NITRILE GROUPS

[75] Inventors: Thomas Himmler; Paul Fiedler, both of Cologne; Rudolf Braden, Odenthal; Hartmuth Buding, Dormagen, all of Fed. Rep. of Germany

[73] Assignee: Bayer Aktiengesellschaft, Leverkusen, Fed. Rep. of Germany

[21] Appl. No.: 930,671

[22] Filed: Nov. 14, 1986

[30] Foreign Application Priority Data

Nov. 26, 1985 [DE] Fed. Rep. of Germany ....... 3541689

[51] Int. Cl.$^4$ ................................................ C08F 8/04
[52] U.S. Cl. ................................ 525/338; 525/329.3; 525/339
[58] Field of Search ................................ 525/338, 339

[56] References Cited

U.S. PATENT DOCUMENTS

| 2,585,583 | 2/1952 | Pinkney | 525/329.3 |
| 3,625,927 | 12/1971 | Yoshimoto et al. | 525/329.3 |
| 4,631,315 | 12/1986 | Buding et al. | 525/329.3 |
| 4,647,627 | 3/1987 | Buding et al. | 525/329.3 |

Primary Examiner—Joseph L. Schofer
Assistant Examiner—Bernard Lipman
Attorney, Agent, or Firm—Connolly and Hutz

[57] ABSTRACT

Unsaturated polymers containing nitrile groups can be hydrogenated with the preservation of the nitrile group in a homogeneous phase with a catalyst of the formula:

$$RuX[(L_1)(L_2)_n]$$

in which
X represents hydrogen, halogen or $SnCl_3$,
$L_1$ represents optionally substituted indenyl,
$L_2$ represents a phosphane, bisphosphane or arsane and n signifies 1 or 2,
if a low-molecular ketone is used as a solvent.

6 Claims, No Drawings

PROCESS FOR THE SELECTIVE HYDROGENATION OF UNSATURATED POLYMERS CONTAINING NITRILE GROUPS

The invention concerns a process for the hydrogenation of unsaturated polymers containing nitrile groups, with the preservation of the nitrile groups.

It is known from U.S. Pat. No. 3,700,637 to homogeneously hydrogenate the CC-double bond of diene-(meth)acrylonitrile copolymers with a large proportion of alternating diene nitrile units with rhodium halogen complex catalysts in chlorobenzene. The suitability of other metals, such as platinum, ruthenium, iridium, palladium, rhenium, cobalt or copper, homogeneously or heterogeneously, is indicated.

In DE-OS No. 2 539 132 a selective hydrogenation of butadiene acrylonitrile copolymers which is dependent on a solvent with the known rhodium catalyst is postulated, in which the CN-triple and cis-double bonds are retained and the vinyl and trans-double bonds are hydrogenated quantitively if chlorobenzene is used as a solvent. In other solvents, in particular ketones, only low degrees of hydrogenation are achieved.

Finally, a method of homogeneously or, preferably, heterogeneously hydrogenating unsaturated polyhydroxy hydrocarbons with molecular weights of up to 4000, whilst the hydroxyl groups are retained with the aid of ruthenium catalysts is known from DE-OS No. 2 459 115. As solvents for the heterogeneous hydrogenation, aliphatic hydrocarbons, aromatic hydrocarbons, alcohols, ethers, esters and water are used; no details are given for homogeneous hydrogenation. The polymers should also be able to contain, for example, acrylonitrile as a comonomer, and detailed descriptions are not given but it must be borne in mind it is known, from U.S. Pat. No. 3,454,664, Example IX, that the nitrile group of benzonitrile is hydrogenated in homogeneous ruthenium catalysis in ethanol to the amino group.

As the occurrence of rhodium is very small and rhodium is used not only in the chemical industry but primarily in the electrical industry, in the glass industry and in the ceramics industry, and very recently particularly in the car industry (exhaust gas catalyst), the possibility that a shortage of this precious metal could arise cannot be ruled out in future.

It was the object of the present invention to provide a new rhodium-independent process for the selective hydrogenation of unsaturated polymers of any structure containing nitrile groups, with the preservation of the nitrile groups, with which a quantitive hydrogenation of all CC-double bonds is achieved if desired, and which gives rise to rubbers with excellent properties for use.

Surprisingly, the object was achieved by the carrying out of a homogeneous reaction using special ruthenium catalysts in special solvents.

The invention provides, therefore, for the hydrogenation of polymers containing nitrile groups in a homogeneous phase with the preservation of the nitrile groups, characterised in that a low-molecular ketone is used as a solvent and a compound of the formula $$RuX[(L_1)(L_2)_n]$$

is used as a catalyst, in which
X represents hydrogen, halogen, $SnCl_3$,
$L_1$ represents optionally substituted indenyl of the formula

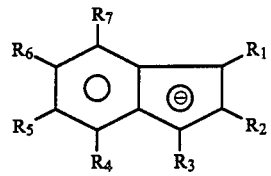

in which $R_1-R_7$ can be the same or different and stand for hydrogen, alkyl residues, cycloalkyl residues, aryl residues or aralykyl residues, in which every two adjacent residues from the $R^1$ to $R^7$ group can also together represent condensed cyclic systems, which optionally contain inert substituents under reaction conditions,
$L_2$ represents a phosphane, bisphosphane or arsane and
n signifies 1 or 2,
X preferably represents hydrogen or chlorine, more preferably $SnCl_3$, $L_1$ preferably indenyl or fluorenyl and $L_2$ preferably a triaryl phosphane.

$L_2$-ligands are, for example, such as correspond to the formulae

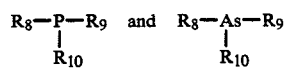

in which $R_8$, $R_9$ and $R_{10}$ can be the same or different, and represent optionally substituted alkyl residues, cycloalkyl residues, aryl residues or aralkyl residues.

Alkyl residues $R_1-R_{10}$ are, for example, straight-chain or branched, saturated hydrocarbon residues with 1 to 20, preferably 1 to 12 and particularly preferably 1 to 6 C-atoms.

Cycloalkyl residues $R_1-R_{10}$ are, for example, cyclic, saturated hydrocarbon residues with 5 to 12, preferably 5 to 7 C-atoms.

Aryl residues $R_1-R_{10}$ are, for example aromatic hydrocarbon residues of the benzene series with 6 to 18, preferably 6 to 12 C-atoms.

Aralkyl residues $R_1-R_{10}$ are, for example, alkyl residues substituted by aryl which consist of a straight-chain or a branched hydrocarbon residue with 1 to 6 C-atoms in the aliphatic part and, in the aromatic part, consist of a residue of the benzene series, preferably phenyl.

The alkyl residues, cycloalkyl residues, aryl residues and aralkyl residues described above can optionally be substituted by hydroxy, $C_1$- to $C_6$-alkoxy, $C_1$- to $C_6$-carbalkoxy, fluorine or chlorine, and the cycloalkyl residues, aryl residues and aralkyl residues can also be substituted by $C_1$- to $C_6$-alkyl.

Preferred $L_2$-ligands are triphenyl phosphane, diethyl phenyl phosphane, tritolyl phosphane, trinaphthyl phosphane, diphenylmethyl-phosphane, tributyl phosphane, tris-(trimethoxyphenyl)-phosphane, bis-(trimethylphenyl,-phenyl phosphane, bis-(trimethoxy phenyl)-phenyl phosphane, trimethyl phenyl-diphenyl phosphane, trimethoxyphenyldiphenyl phosphane, tris-(dimethyl phenyl)phenyl phosphane, bis-(dimethoxy phenyl)-phenyl phosphane, dimethyl phenyl diphenyl phosphane, dimethoxy phenyl diphenyl phosphane, triphenyl arsane, ditolyl phenyl arsane, tris-(4-ethoxy phenyl)-arsane, diphenyl cyclohexyl arsane, dibutyl phenyl arsane and diethyl phenyl arsane.

Other examples of L₂-ligands are afforded by bisphosphanes, of the formula

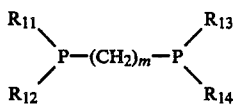

in which m stands for a whole number of 1 to 10 and the residues $R_{11}$–$R_{14}$ have the significance of $R_1$.

Examples of bisphosphanes are afforded by 1,2-bis-diphenyl phosphano butane, 1,2-bis-dianisyl phosphano ethane, preferably 1,3-bis-diphenyl phosphano propane and, in particular, 1,2-bis-diphenyl phosphano ethane.

The ruthenium complexes used are known (L. A. Oro, M. A. Ciriano, M. Campo, C. Foces-Foces and F. H. Cano, J. Organomet. Chem. 289 (1985) 117–131; DE-OS No. 33 37 294) and, for example, can be obtained by the reaction of $RuCl_2(L_2)_3$ with an excess of the ligand $L_1$ in ethanol, with the addition of KOH.

Ruthenium complexes with X=bromine or iodine can be obtained for example, simply by the heating of the corresponding ruthenium complexes of the formula with X=hydrogen with HBr or HI in methanol (cf. T. Wilczewsky, M. Bochenska, J. F. Biernat in J. Organomet. Chem. 215 (1981), pages 87 to 96).

In particular, acetone, butanone, pentanones, cyclopentanone and cyclohexanone are used as solvents for the hydrogenation.

Both the unsaturated and the hydrogenated polymers should be soluble in the solvent used.

The process is suitable for the hydrogenation of copolymers made of 85 to 50% by weight, preferably 82 to 55% by weight of at least one conjugated diene, 15 to 50% by weight, preferably 18 to 45% by weight of at least one unsaturated nitrile and 0 to 10% by weight, preferably 0 to 8% by weight of at least one other monomer which can be copolymerized with conjugated dienes and unsaturated nitriles.

For example buta-1,3-diene, 2-methyl buta-1,3-diene, 2,3-dimethyl buta-1,3-diene and penta-1,3-diene, are used as conjugated dienes, and acrylonitrile and methacrylonitrile are used as unsaturated nitriles.

Vinyl aromatic substances such as styrene, o-, m- or p-methyl styrene, ethyl styrene, vinyl naphthaline and vinyl pyridine, $\alpha,\beta$-unsaturated mono carboxylic acids with 3 to 5 C-atoms such as acrylic acid, methacrylic acid and crotonic acid can be used as the other monomers, as well as $\alpha,\beta$-unsaturated dicarboxylic acids with 4 to 5 C-atoms such as maleic acid, fumaric acid, citraconic acid and itaconic acid, as well as vinyl chloride, vinylidene chloride, N-methylol acrylamide and vinyl alkyl ether with 1 to 4 C-atoms in the alkyl portion.

Preferably a binary copolymer made of butadiene and acrylonitrile is hydrogenated.

The molecular weight of the polymers is not critical and is between 500 and 500,000 g per mol, preferably between 1000 and 200,000 g per mol and, in particular, between 30,000 and 150,000 g per mol (number average, determined by gelpermeation chromatography).

The degree of hydrogenation (percentage of the hydrogenated CC-double bonds related to the total number of the CC-double bonds which were originally present in the polymer) can be up to 100%. The hydrogenation can, however, be interrupted beforehand if necessary. Preferably polymers with a degree of hydrogenation of at least 80%, more preferably of at least 90% are prepared according to the process of the invention. The degree of hydrogenation is determined by means of NMR- and IR-spectroscopy.

The concentration of catalyst, related to polymer (calculated as ruthenium), is 10 to 1000, preferably 10 to 600 ppm, more preferably 40 to 500 ppm. The concentration of unsaturated polymer, related to the total solution, is 1 to 90, preferably 5 to 40% by weight.

The hydrogenation should be carried out at 80° to 200° C., preferably at 100° to 180° C., in particular at 120° to 160° C. and 20 to 350 bar, preferably at 30 to 250 bar hydrogen pressure.

After the hydrogenation process the polymer is separated from the solution using the usual methods, for example, (vacuum)-evaporation, by the injection of water vapour or by the addition of a non-solvent. A drying process follows for the purpose of removing residual solvent or water.

The polymers hydrogenated according to the invention are hardened in the usual manner by peroxide or sulphur vulcanization provided that the vulcanization is not carried out by means of cross-linking by irridation.

On the basis of their excellent resistance to weather, ozone, oil and hot air, and their resistance to wear in a cold climate, these polymers can be used for high-grade rubber articles such as seals, hoses, membranes, for cable insulations and cable converings.

EXAMPLE 1

A solution of 160 g of a statistical butadiene acrylonitrile copolymer with 34.9% by weight acrylonitrile and a Mooney viscosity of ML 1+4 (100° C.) of 29 in 1.6 kg acetone, which solution had been carefully rinsed with nitrogen, was placed in a 3-liter autoclave under nitrogen rinsing. Furtheron under nitrogen a solution which had also been rinsed with nitrogen, of 350 mg $RuH(PPh_3)_2$ ($\eta^5$-$C_9H_7$) in 55 g acetone was added and a pressure of 80 bar hydrogen was imposed.

The mixture was heated to 135° C. and the reaction was continued for 6 hours at 140 bar hydrogen pressure. The degree of hydrogenation of the polymers was determined as 95%.

EXAMPLE 2 AND 3

In accordance with example 1 hydrogenation processes were carried out in acetone at 135° C. with 200 or 300 ppm ruthenium in the form of various complexes. The results are shown in Table 1.

TABLE 1

| Example | Catalyst | ppm Ru | $P_{H_2}$[bar] | D.Hyd. |
|---|---|---|---|---|
| 2 | $RuCl(PPh_3)_2(\eta^5$-$C_9H_7)$ | 200 | 140 | 90 |
| 3 | $RuCl(dppe)$ ($\eta^5$-$C_9H_7$) | 300 | 180 | >99 |
| 4 | $Ru(SnCl_3)(PPh_3)_2(\eta^5$-$C_9H_7)$ | 200 | 180 | 98 |
| 5 | $Ru(SnCl_3)(PPh_3)_2(\eta^5$-$C_{13}H_9)$ | 200 | 140 | 92 |

D.Hyd: degree of hydrogenation
dppe: $Ph_2P$ $(CH_2)_2PPh_2$

We claim:

1. A process for the selective hydrogenation of unsaturated polymers containing nitrile groups in a homogeneous phase with the preservation of the nitrile groups, characterised in that a compound of the formula $RuX[(L_1)(L_2)_n]$ is used as a catalyst, in which
X represents, $SnCl_3$, $L_1$ represents an optionally substituted indenyl of the formula

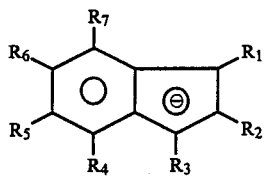

$L_2$ represents a phosphane, bisphosphane or arsane,
$R_1$ to $R_7$ can be the same or different, and stand for hydrogen, alkyl residues, cycloalkyl residues, aryl residues or aralkyl residues, in which every two adjacent residues from the $R^1$ to $R^7$ group can also together represent condensed cyclic systems, which optionally contain inert substituents under reaction conditions,
n signifies 1 or 2
and a low-molecular ketone is used as the solvent.

2. A process according to claim 1, wherein $L_1$ represents indenyl or fluorenyl, $L_2$ represents a triaryl phosphane.

3. A process according to claim 1, wherein $L_2$ represents triphenyl phosphane.

4. A process according to claim 1 or 2, wherein degrees of hydrogenation of 80 to 100% are achieved.

5. A process according to claim 1, wherein $L_2$ represents bisdiphenylphosphinoethane (dppe).

6. A process according to any one of claims 1, 2 or 3, wherein the hydrogenation process is carried out at 80° to 200° C. and 20 to 350 bar hydrogen pressure with a catalyst concentration, related to polymer, calculated as ruthenium, of 10 to 1000 ppm.

* * * * *